(12) United States Patent
Kim

(10) Patent No.: US 10,376,200 B2
(45) Date of Patent: Aug. 13, 2019

(54) SYSTEM FOR DETECTING AND LOGGING OF FLATULENCE FOR HEALTH INDICATION

(71) Applicant: Hong Min Kim, Toronto (CA)

(72) Inventor: Hong Min Kim, Toronto (CA)

( * ) Notice: Subject to any disclaimer, the term of this patent is extended or adjusted under 35 U.S.C. 154(b) by 56 days.

(21) Appl. No.: 15/732,160

(22) Filed: Sep. 28, 2017

(65) Prior Publication Data

US 2019/0090804 A1 Mar. 28, 2019

(51) Int. Cl.
| | |
|---|---|
| *A61B 5/00* | (2006.01) |
| *B01D 53/04* | (2006.01) |
| *B01J 20/20* | (2006.01) |
| *A61L 9/014* | (2006.01) |
| *A61B 10/00* | (2006.01) |
| *G01N 33/48* | (2006.01) |

(52) U.S. Cl.
CPC ............... *A61B 5/42* (2013.01); *A61B 10/00* (2013.01); *A61L 9/014* (2013.01); *B01D 53/0407* (2013.01); *B01J 20/20* (2013.01); *G01N 33/48* (2013.01); *A61B 2010/0083* (2013.01); *A61L 2209/22* (2013.01); *B01D 2253/102* (2013.01); *B01D 2257/304* (2013.01)

(58) Field of Classification Search
CPC ... A61B 5/42; A61B 10/00; A61B 2010/0083; G01N 33/48; A61L 9/014; A61L 2209/22; B01J 20/20; B01D 53/0407; B01D 2257/304; B01D 2253/102
USPC ........................................................ 73/31.07
See application file for complete search history.

(56) References Cited

U.S. PATENT DOCUMENTS

| | | | | |
|---|---|---|---|---|
| 7,559,610 | B1 * | 7/2009 | Hong Min ............. | A47C 7/744 297/180.1 |
| 2011/0319004 | A1 * | 12/2011 | Kim ....................... | A47C 7/744 454/75 |
| 2017/0215787 | A1 * | 8/2017 | Burke ................... | A61B 5/0002 |
| 2017/0278373 | A1 * | 9/2017 | Ansley .................. | G08B 25/08 |
| 2017/0339911 | A1 * | 11/2017 | Fitch ..................... | A01K 1/011 |

* cited by examiner

*Primary Examiner* — Marrit Eyassu
(74) *Attorney, Agent, or Firm* — David W. Wong

(57) ABSTRACT

A system is provided for collecting and logging the frequency of flatulence of a person in a selected time period as well as the duration of each occurrence of flatulence. The log entries provide determination of the body cells signaling of the person indicative of the person's health condition whereby underlying diseases may be detected and treated in their early stage.

5 Claims, 1 Drawing Sheet

SYSTEM FOR DETECTING AND LOGGING OF FLATULENCE FOR HEALTH INDICATION

BACKGROUND OF THE INVENTION

1. Field of the Invention

This invention relates to a system for detecting, logging, and verifying flatulence to provide indication of health condition. It can provide a convenient and easily operated means for monitoring health condition and early discovery of any potential underlying diseases.

2. Background Art

Gas is produced in the gastrointestinal tract of human by symbiotic bacteria and yeast. On the average, human passes gas or flatulence between 10 to 18 times a day. The flatulence generally consists of 20 to 90% of nitrogen, 0 to 50% of hydrogen, 10 to 30% of oxygen, 0 to 10% of methane, and non-typical gases such as hydrogen sulfide ($H_2S$). The molecules of hydrogen sulfide gas in the flatulence carry a number of signaling functions of cells in the human body, which can indicate health conditions. Such cell signaling has been extensively studied in the context of human diseases. It has been found that the bacteria in the human gastrointestinal tract exchange signals with each other and with the immune system cells. The molecular signal of the hydrogen sulfide gas in the flatulence directly relates to the gastrointestinal tract bacterial exchange signals. Therefore, detecting and logging the frequency and the intensity represented by the duration of time gases are released in the flatulence can provide information of the bacterial cell signaling activity indicative of the general health condition and/or the need for seeking further medical attention for finding possible underlying diseases. Many diseases can be treated and cured if detected in their early stage. Thus, the present system provides an effective cautionary device for the early discovery of possible diseases.

SUMMARY OF THE INVENTION

A principal object of the present invention is to provide a system for detecting, logging, and verifying flatulence by detecting the activity of hydrogen sulfide molecular signaling in the flatulence to provide indication of health condition.

Another object of the present invention is to provide a system for detecting and logging the frequency of flatulence.

Another object of the present invention is to provide a system for detecting the duration of time of each occurrence of flatulence.

Yet another object of the present invention is to provide a system for displaying the result of the detection of flatulence to derive a visual indication of health condition.

Briefly, the system comprises a gas collecting device mountable under a sitting means for receiving flatulence released by a user sitting on the sitting means. A hydrogen sulfide sensor is connected to or located directly inside the gas collecting device, which is operative for detecting existence of hydrogen sulfide gas in the flatulence. A frequency detector is connected to the hydrogen sulfide sensor for detecting how often flatulence is released by the user in a selected period of time. A duration detector is also connected to the hydrogen sulfide sensor for detecting the duration of each occurrence of flatulence. A logging device is connected to the frequency detector and is operative for receiving an event signal from the frequency detector indicative of the number of times flatulence occur in the selected period of time; and simultaneously the duration device also forward a duration signal to the logging device indicative of the length of time of each occurrence of the flatulence. A display device connected to the logging device. The display device and the logging device are operative by a user panel for displaying entries of the occurrence of frequency of occurrence of flatulence and duration of occurrence of each flatulence in the selected logging period of time. The logging entries represent body cells signaling activity indicative of health condition and the requirement of further medical attention for finding any possible underlying diseases.

DETAILED DESCRIPTION OF THE PREFERRED EMBODIMENTS

Figure 1:
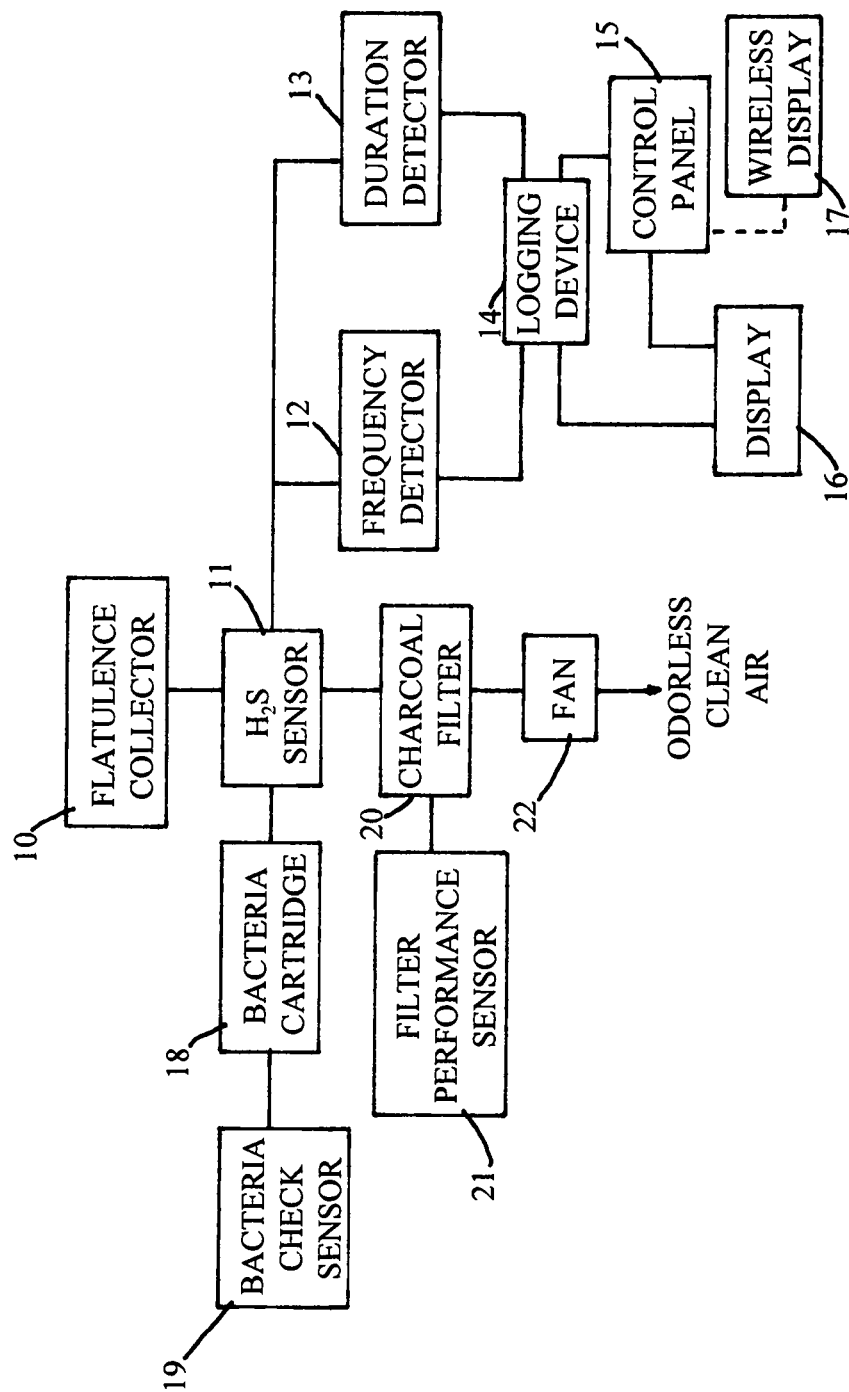
FIG. 1 is a block diagram showing the construction of the system of the present invention.

With reference to the drawing, a flatulence collector 10 which may be provided in the seat area of a chair, or underneath a toilet seat and the like for receiving the flatulence released by a person sitting thereon. The collector is preferably bell-shaped having an open-top frusto-conical or cup-shaped casing with a conducting tube connected to its bottom end. The collector 10 can be located underneath the seat cover of the chair with the upper rim of the collector 10 butting against the under-surface of the seat cover of the chair. Openings are formed in the seat cover so that gas released in flatulence by a person sitting on the chair would directly enter and fill the collector 10. The conducting tube conducts the flatulence from the collector 10 to a hydrogen sulfide sensor 11, or alternatively the hydrogen sulfide sensor 11 may be directly mounted within the collector 10, for detecting the existence of $H_2S$ (hydrogen sulfide) gas in the flatulence. A frequency detector 12 is connected to the hydrogen sulfide sensor 11. The frequency detector 12 will generate an event signal each time gas containing hydrogen sulfide is released by the person sitting on the chair. Also, a duration sensor 13 is connected to the hydrogen sulfide sensor 11 by the conducting tube for detecting the length of time of each flatulence. The frequency detector 12 sends an event signal to a logging device 14 which records the number of times flatulence occurs within a selected period of time, for example, in a 24 hours period over several recording days. Simultaneously, the duration sensor 13 also sends a duration signal to the logging device 14 to provide the information of the length of time of each flatulence.

A user panel 15 is connected to the logging device 14 and a display 16 such that the user can operate the control panel 15 to display the recorded entries of the frequency and duration of each flatulence over a time period selected by the user. The display 16 may be located on the chair. Alternatively, the entries may be forwarded wirelessly to show the recorded data in a remote display 17.

A printed report of the log entries may also be generated by a printer (not shown) connected to the logging device 14 to provide a printed report of the log entries.

The combination of the correlated log entries of the frequency and duration of the flatulence over a selected period of time would indicate the molecule signaling of the $H_2S$ (hydrogen sulfide) in the flatulence.

When the display and/or the printed report show a regular pattern of occurrence of hydrogen sulfide in the flatulence, it would indicate normal body cell signaling and normal health condition. When the display shows an irregular pattern of occurrence of hydrogen sulfide gas in the flatulence, or unusually high frequency of occurrence, or long duration of occurrence, it would indicate occurrence of irregular body cell signaling, so that further medical attention and investigation would be required to determine whether the irregular results are due to underlying diseases.

As the pattern of flatulence varies for each person, a normal pattern can first be established by logging the flatulence occurrence over a certain selected period of time, for example, 5 days.

Following is an example of log results of a normal flatulence pattern recorded over a five days period:

| Number of occurrence | Day of occurrence | Time of occurrence | Duration of flatulence |
|---|---|---|---|
| $1^{st}$ | Monday | 10:17 am | 1 min |
| $2^{nd}$ | Monday | 1:43 pm | 1 min |
| $3^{rd}$ | Monday | 2:06 pm | 2 min |
| $1^{st}$ | Tuesday | 11:34 am | 1 min |
| $2^{nd}$ | Tuesday | 3:27 pm | 1 min |
| Nil | Wednesday | | |
| $1^{st}$ | Thursday | 9:51 am | 2 min |
| $2^{nd}$ | Thursday | 10:02 am | 3 min |
| $3^{rd}$ | Thursday | 11:17 am | 2 min |
| $4^{th}$ | Thursday | 1:22 pm | 1 min |
| $1^{st}$ | Friday | 1:51 pm | 1 min |
| $2^{nd}$ | Friday | 4:12 pm | 2 min |

In the above exemplary log results, they indicate flatulence occur in regular frequency and duration so that there is no medical concern.

Following is an example of log results showing an abnormal flatulence pattern over a short period of 1 day:

| Number of occurrence | Day of occurrence | Time of occurrence | Duration of occurrence |
|---|---|---|---|
| $1^{st}$ | Monday | 8:09 am | 4 min |
| $2^{nd}$ | Monday | 8:18 am | 6 min |
| $3^{rd}$ | Monday | 8:27 am | 6 min |
| $4^{th}$ | Monday | 8:35 am | 5 min |
| $5^{th}$ | Monday | 8:52 am | 9 min |

In the above exemplary log results, they indicate detection of hydrogen sulfide gas in the flatulence occurring in a short period of time with unusually long duration in each occurrence. Repetitive showing of such log results would warrant further medical attention and investigation to find out whether it is due to any possible underlying disease.

The hydrogen sulfide ($H_2S$) sensor 11 is provided with a removable bacteria cartridge 18, and a bacteria check sensor 19 is connected to the removable bacteria cartridge 18. After each logging session, the bacteria cartridge 18 can be removed and cleaned, or when the bacteria check sensor 19 detects accumulation of hydrogen sulfide molecule in the hydrogen sulfide sensor 11, so that it is necessary to remove and clean the removable bacteria to ensure the accuracy of the hydrogen sulfide sensor for the subsequent operation of the system.

The flatulence after passing through the hydrogen sulfide sensor 11 will flow through a removable charcoal filter 20 to eliminate the obnoxious smell of the hydrogen sulfide gas. A filter performance sensor 21 is connected to the charcoal filter 20 to detect the cleanliness of the charcoal filter 20 so as to determine whether the charcoal filter 20 should be removed and cleaned or replaced.

A fan or blower 22 is connected to the charcoal filter 20 at the exit end of the system to assist the drawing of the flatulence to flow through the entire system.

After passing through the charcoal filter 20, the flatulence becomes an odorless clean air which may then be released into the atmosphere without causing pollution to the atmosphere.

The system of the present invention is normally not in operation until it is turned on by the user operating the user control panel 15 to acuate the logging device 14 so that the system is not in operation in the event an unintended user sits on the chair or toilet equipped with this system. Furthermore, the logging device 14 includes a plurality of logging files assigned to multiple users using the chair or toilet seat equipped with the present system. The control 15 may be operated to select the logging file assigned for logging the flatulence of the particular user and display the log entries of that particular user on the display.

The system of the present invention may be retrofitted or integrally incorporated in a chair or a toilet seat with the user operating panel provided on the arm rest of the chair or mounted to the toilet seat.

What is claimed is:

1. A system for detecting and logging the occurrence of flatulence comprising:
   a gas collecting device mounted underneath a seat for receiving flatulence released by a user sitting on said seat;
   a hydrogen sulfide sensor located within said gas collecting device and connected to said gas collecting device and operative to detect existence of hydrogen sulfide gas in said flatulence;
   a frequency detector connected to said hydrogen sulfide sensor for detecting frequency of occurrence of flatulence in a selected period of time;
   a duration detector connected to said hydrogen sulfide sensor for detecting duration of each occurrence of flatulence;
   a logging device connected to said frequency detector and operative for receiving an event signal from said frequency detector indicative of number of times flatulence occurring in said selected period of time; and said duration device also forwarding a duration signal to said logging device indicative of the length of time of each occurrence of the flatulence;
   a removable bacteria cartridge connected to said hydrogen sulfide sensor and a bacteria check sensor connected to said removable bacteria cartridge and operative for indicating whether said bacteria cartridge is to be removed for cleaning to remove accumulation of bacteria in said removable bacteria cartridge;
   a display device connected to said logging device, said display device and said logging device being operative by a user control panel connected to said logging device and said display device to display entries of said occurrence of frequency of occurrence of flatulence and duration of occurrence of each flatulence in said selected logging period of time for representing body cells signaling activity indicative of health condition of said user.

2. A system according to claim 1 including a charcoal filter connected to said removable bacteria cartridge, and a filter performance sensor connected to said charcoal filter, and said filter performance sensor being operative to determine the operation of said charcoal filter for removing obnoxious odor of the flatulence.

3. A system according to claim 2 further comprising a blower fan located at an exit end of said system and operative for enhancing the flow of flatulence through said system.

4. A system according to claim 3 wherein said user control panel is operative for turning said system on and off.

5. A system according to claim 3 wherein said logging device includes a plurality of logging files assigned to logging flatulence with each file assigned for logging results of flatulence of a different particular individual user, and said user control panel is operative to select the particular assigned file for logging the results of flatulence occurrences of that particular individual user.

* * * * *